United States Patent [19]

Tatsuoka et al.

[11] Patent Number: 5,401,850
[45] Date of Patent: Mar. 28, 1995

[54] CYCLOPROPACHROMEN DERIVATIVES

[75] Inventors: Toshio Tatsuoka, Hyogo; Kayoko Nomura, Osaka; Yuzo Nakagawa, Tochigi; Shizuo Nakamura, Osaka, all of Japan

[73] Assignee: Suntory Limited, Tokyo, Japan

[21] Appl. No.: 15,030

[22] Filed: Feb. 8, 1993

Related U.S. Application Data

[63] Continuation-in-part of Ser. No. 662,107, Feb. 28, 1991, abandoned.

[51] Int. Cl.$^6$ .................. C07D 413/12; A61K 31/35; A61K 31/44
[52] U.S. Cl. ..................... 546/269; 549/385
[58] Field of Search .................. 546/269; 549/385; 514/454, 337

[56] References Cited

U.S. PATENT DOCUMENTS 4,713,453 12/1987 Tatsuoka et al. .................. 544/60
5,155,129 10/1992 Tatsuoka ..................... 514/454

FOREIGN PATENT DOCUMENTS 238883 9/1987 European Pat. Off. .

Primary Examiner—C. Warren Ivy
Assistant Examiner—D. Margaret M. Mach
Attorney, Agent, or Firm—Cushman, Darby & Cushman

[57] ABSTRACT

A cyclopropachromen derivative represented by formula (I):

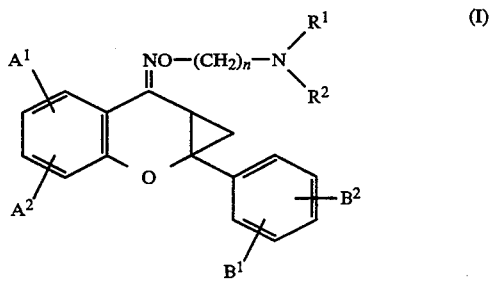

The compounds are capable of promoting the extension of nerve dendrites and are useful as improving and treating agents for cerebral organic disorders and psychic function disorders.

7 Claims, No Drawings

CYCLOPROPACHROMEN DERIVATIVES

This is a continuation-in-part application of U.S. Ser. No. 07/662,107, filed on Feb. 28, 1991, now abandoned.

FIELD OF THE INVENTION

This invention relates to a novel cyclopropachromen derivative represented by formula (I) shown below and a pharmaceutically acceptable salt thereof.

The compounds according to the present invention have a wide use as improving and treating agents for cerebral organic and functional disorders.

BACKGROUND OF THE INVENTION

Organic and functional disorders in the human brain which controls high grade mental actions and motor functions are critical diseases that concern not only the physical but also the mental well-being of a person. In a rapidly aging society, the development of effective methods of treating brain disorders as well as therapeutic drugs is of pressing importance. However, despite many years of studies conducted to unravel the functions of the brain, only a partial understanding has so far been achieved and an understanding of individual diseases, still less a comprehensive and systematic knowledge of the brain, has not yet been obtained.

While many brain diseases are known today, Alzheimer's disease (hereinafter sometimes abbreviated as AD) and senile dementia of the Alzheimer's type (hereinafter sometimes referred to as SDAT), both of which are progressive organic diseases of the brain that are characterized by lowered cognitive capabilities due to the degenerative atrophy of neurocytes in the brain, are becoming major social concerns requiring the implementation of effective care methods since the number of patients suffering from these diseases, especially in industrialized countries is rapidly increasing, and the progression of these diseases results in severe disability and ultimate death for those afflicted.

Under these circumstances, industrialized countries are engaged in nationwide projects for the establishment of effective methods for treating AD and SDAT. However, even the causes of the diseases have not been properly elucidated. Only the morphological changes that can be observed in the brain or the biochemical changes as the consequences have been partly unravelled, but no effective therapy has yet been established.

Cholinergic agents including choline precursors, cholinesterase inhibitors, etc. are being tested, on the basis of the cholinergic theory, in clinical fields as nosotropic agents for treating AD and SDAT. However, the evaluation on the utility of these therapeutics is varied and no single drug exhibits definite therapeutic effects.

Three basic methods may be conceived of to treat neurodegenetative diseases including AD and SDAT: (1) suppressing or preventing the degenerative process of neurons; (2) compensating for the lost function of neurons with a drug; and (3) promoting the plasticity of remaining neurons to form a new neuro-circuit. The aforementioned cholinergic agents and chollnesterase inhibitors are within the class (2) since they are focused on the fact that, in a characteristic pathological symptom of AD and SDAT, cholinergic nerve fascicles that project from the basal forebrain to the cerebral cortex and the hippocampus undergo atrophic degeneration, yet acetylcholine receptors in the cerebral cortex and the hippocampus which are the cells that control those cholinergic nerve fascicles remain in a normal state. These drugs are expected to work effectively in the case of dysfunction of acetylcholine systems but no definite therapeutic effects are anticipated for diseases such as AD and SDAT which cannot be fully explained solely on the basis of the dysfunction of acetylcholine systems.

Aggravation of brain diseases could be prevented if the degenerative process of neurons could be suppressed as in (1). If a new neuron network could be formed by promoting the compensatory functional recovery of remaining neurons as in (3), not only could the progress of the diseases be prevented but also positive recovery of neuro-functions could reasonably be expected.

A drug that has been proposed in line with these approaches is a nerve growth factor (which is hereinafter referred to as "NGF"). NGF has long been known as a factor that is essential to the existence of sympathetic ganglion and sensory ganglion neurons in the peripheral nervous system, and hence extensive studies have been conducted on NGF. Recently, it has become clear that NGF also takes part in the existence and sustained functions of cholinergic neurons in the basal forebrain which are important to memory and learning. Thus the possibility of using NGF as an effective means of recovering part of the brain functions has been studied. However, NGF is a basic protein having a molecular weight of ca. 27,000 and the efforts to develop a direct method of compensatory therapy using NGF have not yet achieved a prospect for application in clinical fields since they involve many problems to be solved as regards the methods of its production and administration.

Under these circumstances, increasing attention has recently been drawn by ganglioside as a non-peptide trophic factor like substance. For example, L. Facci et al. reported in J. Neurochem., 42, 299–305 (1985) that monosialoganglioside ($GM_1$) promoted the formation of nerve dendrites in cultured cells derived from mouse neuroblasts. L. F. Agnati et al., Acta Physiol. Scand., 119, 347–364 (1983) and G. Toffano et al., Brain Res., 296, 233–239 (1984) reported that $GM_1$ inhibited the degeneration of the cell body of nigra dopamine neurons that occurred after the removal of the cortex on one side of the brain. Further, G. Jonsson et al. reported in Neurosci. Lett. (Suppl.), 14, 185 (1983) that $GM_1$ worked suppressively on the decrease in 5-HT in the frontal and occipital lobes that was caused by pretreatment with 5,7-dihydroxytryptamine. These reports did not make it clear whether the action of ganglioside was direct or indirect in relation to the intermediary of the neurotrophic factor in NGF but they did show that ganglioside had the ability to either inhibit the degeneration of neurons or promote the compensatory functional recovery of a degenerated nerve circuit. Therefore, these observations suggest the possibility of new pharmaceutical therapy of AD and SDAT.

In fact, however, ganglioside is a glycosphingolipid containing sialic acid and $GM_1$, too, is a high-molecular weight compound that is the condensate of sialic acid, four saccharides and ceramide. Hence, the use of ganglioside as a drug for treating AD and SDAT involves several problems to be solved in terms of the methods of preparation and administration.

SUMMARY OF THE INVENTION

Under these circumstances, the present inventors conducted intensive studies and found novel compounds that were easy-to-synthesize. They are low molecular weight compounds that are capable of promoting the extension of nerve dendrites and that are as effective as NGF and ganglioside in suppressing the degenerative process of nerves or regenerating a damaged nerve network to promote the recovery of its functions.

Further, the novel cyclopropachromen derivatives of the present invention exhibit cerebral function improving activities in experimental model animals suffering from various cerebral anoxemic conditions even at low dose levels and are, therefore, effective in alleviating and treating organic and functional disorders.

The present invention provides a cyclopropachromen derivative represented by formula (I):

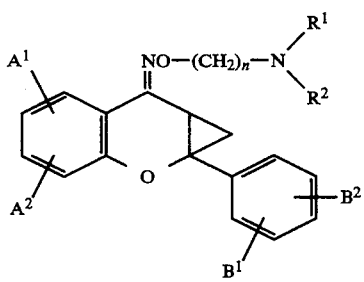

wherein
n represents an integer of 2 to 5;
one of $R^1$ and $R^2$ represents a hydrogen atom or an alkyl group having 1 to 5 carbon atoms, a phenyl group or an aralkyl group having 7 to 10 carbon atoms, and the other of $R^1$ and $R^2$ represents an alkyl group having 1 to 5 carbon atoms, a phenyl group or an aralkyl group having 7 to 10 carbon atoms, or
$R^1$ and $R^2$ form together with the nitrogen atom, to which they are attached, a morpholino group, a thiomorpholino group, pyrrolidinyl group, a piperidinyl group, a homopiperidinyl group, a piperazinyl group, a homopiperazinyl group, an N-alkylpiperazinyl group, N-alkylhomopiperazinyl group, an N-hydroxyalkylpiperazinyl group or a pyrrolidonyl group or alternatively $R^1$ and $R^2$ form together with the nitrogen atom to which they are attached, and further a carbon atom to which said nitrogen atom is bound, a pyrrolitydinyl group of formula:

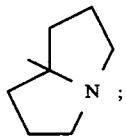

$A^1$ and $A^2$ independently represent a hydroxyl group, a halogen atom, an alkoxy group having 1 to 10 carbon atoms or an alkoxy group having 1 to 10 carbon atoms substituted with phenyl or pyridyl;
$B^1$ and $B^2$ independently represent a hydrogen atom, a hydroxyl group, a halogen atom, an alkoxy group having 1 to 10 carbon atoms or an alkoxy group having 1 to 10 carbon atoms substituted with phenyl or pyridyl, and a pharmaceutically acceptable salt thereof.

The term "halogen" as used herein includes fluoro, chloro, bromo or iodo, and fluoro, chloro and bromo are preferred.

The integer represented by n is preferably 2–4 and more preferably 2 or 3.

Examples of the alkyl group represented by $R^1$ and $R^2$ may be straight or branched. Those having 1–3 carbon atoms such as methyl and ethyl are preferred.

Examples of the aralkyl group represented by $R^1$ and $R^2$ include benzyl, phenethyl.

When $R^1$ and $R^2$ form together with the nitrogen atom, to which they are attached, an N-alkylpiperazinyl group or an N-hydroxyalkylpiperazinyl group, examples of the alkyl moiety include methyl, ethyl and propyl.

When $A^1$, $A^2$, $B^1$ and $B^2$ represent an alkoxy group, it has preferably 1 to 5 carbon atoms.

It should be understood that the compound of the present invention comprises several isomers as schematically illustrated below. Namely, there are two geometrical isomers (E-form and Z-form) at the oxime structure, and further, each of the geometrical isomers has two optical isomers. Each isomers can be separated by a conventional manner by way of, e.g. recrystallization, column chromatography, TLC, HPLC or by using a chemical substance commonly used in the separation of optical isomers.

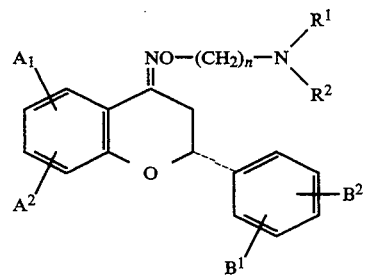

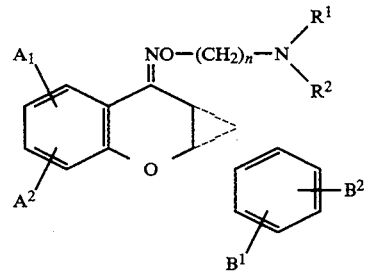

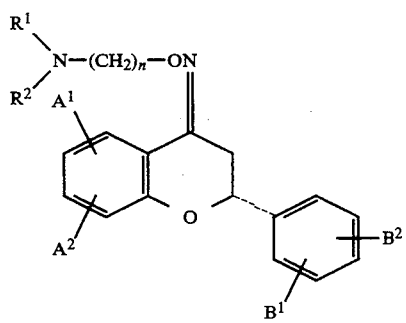

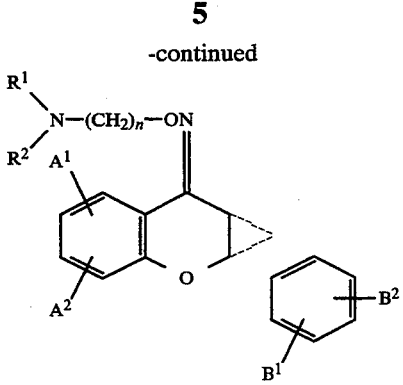

DETAILED DESCRIPTION OF THE INVENTION

The compounds represented by formula (I) can be synthesized in accordance with the process described in Japanese Patent Application Laid-Open No. Sho-62-198676 as illustrated by the following reaction scheme:

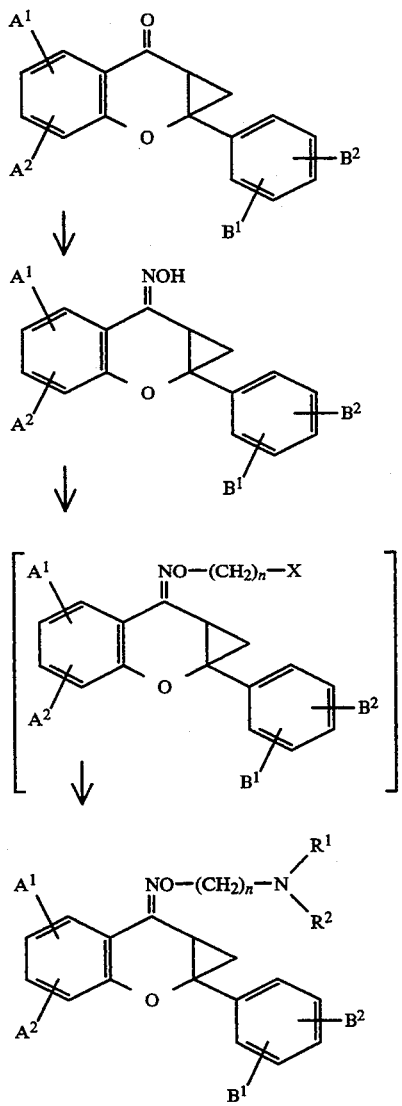

Compound (II) is reacted with hydroxylamine hydrochloride in pyridine to obtain compound (III). Compound (III) is then condensed with a halogenated amine compound of formula:

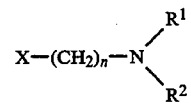

wherein $R^1$, $R^2$ and n are as defined above; and X represents a halogen atom, to obtain compound (I).

Alternatively, compound (III) is condensed with a bifunctional compound represented by formula:

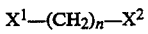

wherein $X^1$ represents a halogen atom; and $X^2$ represents a halogen atom or an ethylene oxide group, to form compound (IV), which is then reacted with an appropriate amine compound to obtain compound (I).

The starting compound (II) is known per se as disclosed in P. Bennett, et al., J. Chem. Soc., Perkin Trans., I, No. 12, p. 2990 (1979) or can be synthesized by the process disclosed therein.

The compounds according to the present invention have low toxicity and can be formulated either as such or as a salt thereof, such as inorganic acid salts (e.g., hydrochloride, sulfate, nitrate, phosphate), organic acid salts (e.g., acetate, propionate, butyrate, tartrate, malonate, succinate, maleate, fumarate, oxalate, citrate, malate, p-toluenesulfonate, methanesulfonate), and alkali metal salts (e.g., sodium salt, potassium salt) in cases where either $A^1$ or $A^2$ is a hydroxyl group, together with known carriers into various preparations for the improvement and treatment of symptoms caused by various disturbances in the brain. For example, the active ingredient is formulated either alone or in combination with commonly employed vehicles, etc. into appropriate dosage forms for oral or non-oral administration, such as capsules, tablets, injectable solutions, etc.

These preparations can be prepared, for example, as follows. Capsules are prepared by mixing a powdered active ingredient with vehicles, e.g., lactose, starch or a derivative thereof, a cellulose derivative, etc., and charging the mixture in gelatin capsules. Tablets are prepared by mixing the active ingredient with the abovementioned vehicles and, in addition, binders, e.g., sodium carboxymethyl cellulose, alginic acid, gum arabic, etc., and water, granulating the mixture if desired, adding lubricants, e.g., talc, stearic acid, etc., to the mixture, and punching the mixture by means of a conventional compressive punching machine. Injectable solutions for non-oral administration are prepared by dissolving the active ingredient in sterilized distilled water or sterilized physiological saline together with dissolving aids and sealing the solution into ampules. If desired, the injectable solutions may contain stabilizers, buffering agents, and so on.

Synthesis of the compounds according to the present invention will be illustrated below by way of Reference Examples and Examples. Reference Examples relate to preparation of starting compounds to be used in the synthesis of the compounds of formula (I). Reference Examples are referred to with a combination of two numbers, in which the first number corresponds to the above-mentioned formula (II) to (IV) [e.g., Reference Example II-1 relates to preparation of compound (II)].

Reference Example II-1

1a, 7a-dihydro-4,5-dimethoxy-1-phenylcyclopropa[b]-chromen-7-(1H)-one

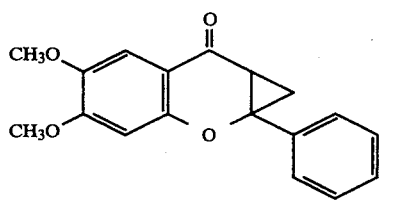

In 100 ml of dimethyl sulfoxide was dissolved 6.78 g (30.8 mmol) of trimethylsulfoxonium iodide, and 1.24 g (30.8 mmol) of sodium hydride (60% oil dispersion) was added to the solution in small portions. The mixture was stirred until evolution of hydrogen ceased. A dimethyl sulfoxide solution having dissolved therein 5.82 g (20.5 mmol) of 6,7-dimethoxyflavone was then added to the reaction mixture, followed by stirring at room temperature for 4 hours. The reaction mixture was poured into ice-water and extracted with diethyl ether. The extract was washed with water and dried over anhydrous magnesium sulfate. After filtration, the filtrate was concentrated, and the residue was purified by silica gel column chromatography using a mixed solvent of hexane-ethyl acetate (70:30) as an eluent to obtain 2.72 g (yield: 44.8%) of the titled compound.

Reference Examples II-2 to II-4

The following compounds were synthesized in the same manner as in Reference Example II-1.

1a,7a-dihydro-3,4-dimethoxy-1a-phenylcylopropa[b]-chromen-7(1H)-one (Reference Example II-2);

4,5-dichloro-1a,7a-dihydro-1a-phenylcyclopropa[b]-chromen-7(1H)-one (Reference Example II-3);

4,5-dibenzyloxy-1a,7a-dihydro-1a-phenylcylopropa[b]-chromen-7(1H)-one (Reference Example II-4).

Physical properties of the compounds obtained in Reference Examples II-1 through II-4 are shown in Table 1 below.

TABLE 1

| Reference Example | Structure | m.p. (°C.) | IR | | NMR |
|---|---|---|---|---|---|
| II-1 | 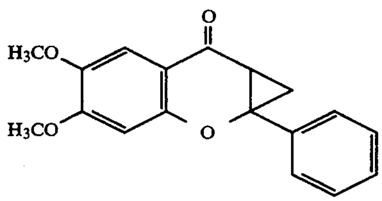 | 146–149 | 3000 1665 1500 1455 1380 1200 1080 1000 810 695 | 2940 1610 1470 1420 1280 1165 1030 960 755 | 1.66(t, 1H, J=6.6Hz) 2.01(dd, 1H, J=6.6Hz & 10.6Hz) 2.47(dd, 1H, J=6.6Hz & 10.6Hz) 3.90(s, 3H), 3.71(s, 3H) 6.52(s, 1H) 7.31–7.49(m, 6H) |
| II-2 | 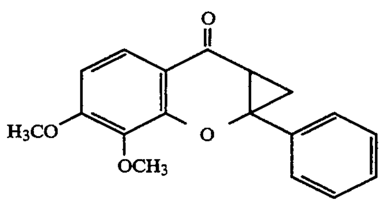 | 105–112 | 2920 1625(br) 1595 1440 1350 1260 1080 780 | 1670(br) 1498 1420 1280 1120 995 | 1.73(t, 1H, J=6.6Hz), 2.00–2.08(m, 1H) 2.50(dd, 1H, J=6.6Hz & 10.9Hz) 3.90(s, 3H), 3.94(s, 3H) 6.71(d, 1H, J=8.6Hz) 7.3–7.5(m, 5H) 7.71 (d, 1H, J=8.6Hz) |
| II-3 | 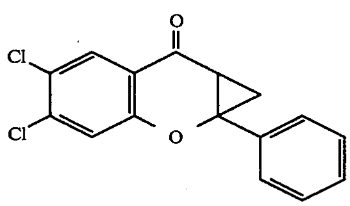 | 108–115 | 1675 1550 1405 1220 975 890 830 | 1598 1445 1260 1120 940 855 680 | 1.54(t, 1H, J=6.6Hz) 2.10(dd, 1H, J=6.6Hz & 10.6Hz) 2.53(dd, 1H, J=6.6Hz & 10.6Hz) 7.21(s, 1H), 7.3–7.5(m, 5H) 8.00(s, 1H) |
| II-4 | 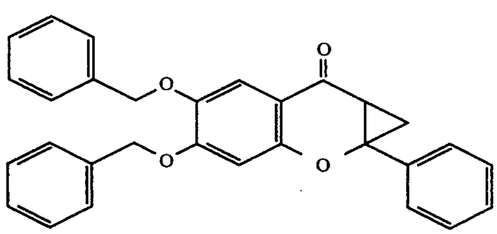 | 124–125 | 1660 1500 1370 1200 1000 820 740 | 1610 1445 1270 1080 865 760 695 | 1.64(t, 1H, J=6.6Hz) 1.99(dd, 1H, J=6.6Hz & 10.6Hz) 2.44(dd, 1H, J=6.6Hz & 10.6Hz) 5.15(s, 2H), 5.18(s, 2H) 6.56(s, 1H) 7.28–7.49(m, 16H) |

Reference Example III-1

1a, 7a-dihydro-4,5-dimethoxy-7 (1H)-hydroxyimino-1a-phenylcyclopropa[b]chromen

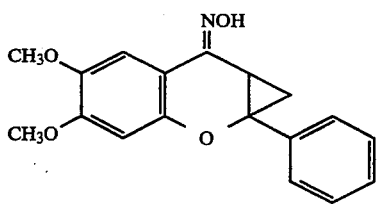

In 50 ml of pyridine was dissolved 500 mg (1.69 mmol) of the compound obtained in Reference Example II-1, and 469 mg (6.76 mmol) of hydroxylamine hydrochloride was added thereto, followed by stirring at 100° C. for 1 hour. The reaction mixture was concentrated, diluted with water, and extracted with chloroform. The chloroform extract was washed with water and dried over anhydrous magnesium sulfate. After filtration, the filtrate was concentrated, and the residue was purified by silica gel column chromatography using a mixed solvent of hexane-ethyl acetate (2:1 by volume) as an eluent to obtain 492 mg (93.6%) of the titled compound.

Reference Examples III-2 to III-4

The following compounds were synthesized in the same manner as in Reference Example III-1.

1a,7a-dihydro-3,4-dimethoxy-7(1H)-hydroxyimino-1a-phenylcyclopropa[b]chromen (Reference Example III-2);

4,5-dichloro-1a,7a-dihydro-7(1H)-hydroxyimino-1a-phenylcyclopropa[b]chromen (Reference Example III-3);

4,5-dibenzyloxy-1a,7a-dihydro-7(1H)-hydroxyimino-1a-phenylcyclopropa[b]chromen (Reference Example III-4).

Physical properties of the compounds obtained in Reference Examples III-1 through III-4 are shown in Table 2 below.

TABLE 2

| Reference Example | Structure | m.p. (°C.) | IR | | NMR |
|---|---|---|---|---|---|
| III-1 | (see figure) | 194–195 | 3200 1615 1440 1380 1255 1160 1035 900 765 | 2820 1505 1420 1305 1210 1080 1010 840 690 | 1.60(t, 1H, J=6.6Hz) 2.13(dd, 1H, J=6.6Hz & 10.6Hz) 2.92(dd, 1H, J=6.6Hz & 10.6Hz) 3.89(s, 3H), 3.92(s, 3H) 6.56(s, 1H) 7.27–7.58(m, 6H) |
| III-2 | (see figure) | 152–153 | 3200 1640 1495 1422 1335 1255 1140 1090 960 825 715 | 2910 1600 1450(br) 1375 1280 1220 1105 1015 855 750 | 1.66(t, 1H, J=6.6Hz) 1.92(dd, 1H, J=6.6Hz & 10.6Hz) 3.14(dd, 1H, J=6.6Hz & 10.6Hz) 3.89(s, 6H) 6.62(d, 1H) 7.25–7.55 (m, 5H) 7.77(m, 1H) |
| III-3 | (see figure) | 136.5–137.5 | 1625 1200(br) | 1405 | 1.60(t, 1H, J=6.6Hz) 1.94(dd, 1H, J=6.6Hz & 10.6Hz) 3.08(dd, 1H, J=6.6Hz & 10.6Hz) 7.13(s, 1H) 7.25–7.5(m, 5H) 7.87(s, 1H) |
| III-4 | (see figure) | 160–161 | 3100 1610 1440 1300 1200 1080 1000 900 750 | 2850 1500 1375 1250 1170 1040 930 840 690 | 1.62(t, 1H, J=6.6Hz) 2.08(dd, 1H, J=6.6Hz & 10.5Hz) 2.90(dd, 1H, J=6.6Hz & 10.5Hz 5.06(s, 2H), 5.12(s, 2H) 6.57 (s, 1H) 7.22–7.54(m, 16H) |

Reference Example IV-1

7(1H)-(2-chloroethyloxymino)-4,5-dimethoxy-1a,7a-dihydro-1a-phenylcycopropa[b]chromen

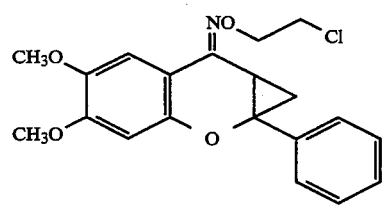

In 20 ml of dioxane was dissolved 300 mg of the compound obtained in Reference Example III-1, and 57.9 mg (1.5 equivalents) of sodium hydride (60% oil dispersion) was added to the solution. Then, 0.482 ml (6 equivalents) of 1-bromo-2-chloroethane was added thereto, and the reaction mixture was heated at 100° C. for 5 hours with stirring, followed by concentration. The residue was diluted with water and extracted with diethyl ether. The diethyl ether layer was washed with water and dried over anhydrous magnesium sulfate. After filtration, the filtrate was concentrated, and the residue was purified by silica gel column chromatography using a mixed solvent of hexane and ethyl acetate (85:15 by volume) as an eluent to obtain 275 mg (76.3%) of the titled compound.

Reference Example IV-2

7(1H)-(3-chloropropyloxyimino)-4,5-dimethoxy-1a,7a-dihydro-1a-phenylcyclopropa[b]chromen The titled compound was synthesized from the compound of Reference Example III-1 in the same manner as in Reference Example IV-1.

Physical properties of the compounds obtained in Reference Examples IV-1 and IV-2 are shown in Table 3 below.

aqueous solution were added to the residue, and the residue was extracted with methylene chloride. The extract was washed with water and dried over magnesium sulfate. After filtration, the filtrate was concentrated, and the residue was purified by silica gel column chromatography using a mixed solvent of methylene chloride and methanol (9:1) as an eluent to obtain 165 mg (62.0%) of the titled compound.

The resulting compound was converted to its L-tartrate in a usual manner.

Example 2

4,5-dichloro-1a,7a-dihydro-7(1H)-(2-dimethylaminoethyloxyimino)-1a-phenylcyclopropa[b]chromen [Compound of formula (I) wherein $A^1 = 4\text{-Cl}$; $A^2 = 5\text{-Cl}$; $B^1 = H$, $B^2 = H$; $NR^1R^2 = N(CH_3)_2$; and $n = 2$]

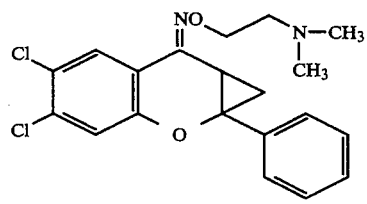

TABLE 3

| Reference Example | Structure | m.p. (°C.) | IR | | NMR |
|---|---|---|---|---|---|
| IV-1 | 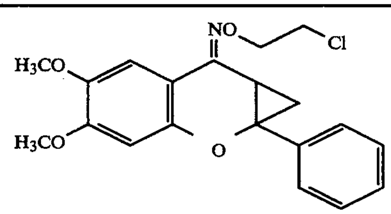 | oil | 2950 | 2840 | 1.57(t, 1H, J=6.6Hz) |
| | | | 1605 | 1500 | 1.89(dd, 1H, J=6.6Hz & 10.6Hz) |
| | | | 1455 | 1425 | 3.02(dd, 1H, J=6.6Hz & 10.6Hz) |
| | | | 1260 | 1220 | 3.81(t, 2H, J=5.9Hz) |
| | | | 1200 | 1170 | 3.87(s, 3H), 3.90(s, 3H) |
| | | | 1085 | 1035 | 4.40(t, 2H, J=5.9Hz) |
| | | | 860 | 805 | 6.50(s, 1H) 7.21–7.49(m, 6H) |
| | | | 760 | 695 | |
| IV-2 | 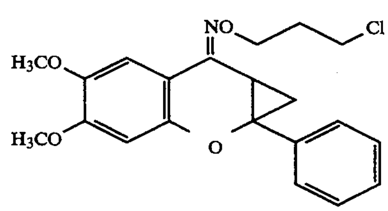 | oil | 2920 | 1620 | 1.56(t, 1H, J=6.6Hz) |
| | | | 1600 | 1500 | 1.87(dd, 1H, J=6.6Hz & 10.5Hz |
| | | | 1465 | 1450 | 2.22(quintet1, 2H, J=6.6Hz) |
| | | | 1420 | 1370 | 2.94(dd, 1H, J=6.6Hz & 10.5Hz) |
| | | | 1300 | 1255 | 3.69(t, 2H, J=6.6Hz) |
| | | | 1210 | 1195 | 3.87(s, 3H), 3.90(s, 3H) |
| | | | 1160 | 1080 | 4.32(t, 2H, J=6.6Hz) |
| | | | 1035 | 865 | 6.49(s, 1H) |
| | | | 805 | 755 | 7.23–7.48(m, 6H) |
| | | | 690 | | |

Example 1

1a,7a-dihydro-4,5-dimethoxy-7(1H)-(2-methylaminoethyloxyimino)-1a-phenylcyclopropa[b]chromen [Compound of formula (I) wherein $A^1 = 4\text{-OCH}_3$; $A^2 = 5\text{-OCH}_3$; $B^1 = H$; $B^2 = H$; $NR^1R^2 = NHCH_3$; and $n = 2$]

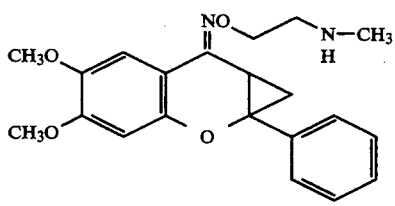

In 10 ml of dioxane was dissolved 270 mg of the compound obtained in Reference Example IV-1, and 10 ml of a saturated mono-methylamine solution in dioxane was added to the solution. The mixture was heated in a closed tube at 100° C. for 17 hours and then freed of dioxane by distillation. Water and a sodium hydroxide In 7 ml of tetrahydrofuran was dissolved 95 mg (0.3 mmol) of the compound obtained in Reference Example III-3, and 18 mg (0.45 mmol) of sodium hydride (60% oil dispersion) was added thereto, followed by stirring at room temperature for 45 minutes. To the reaction mixture was added 128 mg (1.19 mmol) of dimethylaminoethyl chloride, followed by refluxing under heating for 17 hours. The reaction mixture was concentrated, and the residue was diluted with ice-water and extracted with diethyl ether. The extract was washed with water and dried over anhydrous magnesium sulfate. After filtration, the filtrate was concentrated, and the residue was purified by neutral silica gel column chromatography using a mixed solvent of methylene chloride and methanol (95:5) as an eluent to obtain 112 mg (99.0%) of the titled compound.

The resulting compound was converted to its maleate in a usual manner. The physical properties of the maleate are shown in Table 4 below.

Example 3

1a,7a-dihydro-4,5-dimethoxy-7(1H)-(2-dimethylaminoethyloxyimino)-1a-phenylcyclopropa[b]chromen [Compound of formula (I) wherein $A^1=4\text{-OCH}_3$; $A^2=5\text{-OCH}_3$; $B^1=H$; $B^2=H$; $NR^1R^2=N(CH_3)_2$; $n=2$]

The titled compound was synthesized from the compound of Reference Example III-1 in the same manner as in Example 2.

Example 4

7(1H)-2-(diethylaminoethyloxyimino)-1a,7a-dihydro-4,5-dimethoxy-1a-phenylcyclopropa[b]chromen [Compound of formula (I) wherein $A^1=4\text{-OCH}_3$; $A^2=5\text{-OCH}_3$; $B^1=H$; $B^2=H$; $NR^1R^2=N(C_2H_5)_2$; $n=2$]

The titled compound was synthesized from the compound of Reference Example III-1 in the same manner as in Example 2.

Example 5

4,5-dichloro-1a,7a-dihydro-7(1H)-(3-methylaminopropyloxyimino)-1a-phenylcyclopropa[b]chromen [Compound of formula (I) wherein $A^1=4\text{-Cl}$; $A^2=5\text{-Cl}$; $B^1=H$; $B^2=H$; $NR^1R^2=NHCH_3$; $n=3$]

The titled compound was synthesized from the compound of Reference Example III-3 in the same manner as in Example 2.

Example 6

1a,7a-dihydro-4,5-dimethoxy-7(1H)-(3-methylaminopropyloxyimino)-1a-phenylcyclopropa[b]chromen [Compound of formula (I) wherein $A^1=4\text{-OCH}_3$; $A^2=5\text{-OCH}_3$; $B^1=H$; $B^2=H$; $NR^1R^2=NHCH_3$; $n=3$]

The titled compound was synthesized from the compound of Reference Example IV-2 in the same manner as in Example 1.

Example 7

4,5-dichloro-1a,7a-dihydro-7(1H)-(3-ethylaminopropyloxyimino)-1a-phenylcyclopropa[b]chromen [Compound of formula (I) wherein $A^1=4\text{-Cl}$; $A^2=5\text{-Cl}$; $B^1=H$; $B^2=H$; $NR^1R^2=NHC_2H_5$; $n=3$]

The titled compound was synthesized from the compound of Reference Example III-3 in the same manner as in Example 2.

Example 8

1a,7a-dihydro-7(1H)-(3-dimethylaminopropyloxyimino)-3,4-dimethoxy-1a-phenylcyclopropa[b]chromen [Compound of formula (I) wherein $A^1=3\text{-OCH}_3$; $A^2=4\text{-OCH}_3$; $B^1=H$; $B^2=H$; $NR^1R^2=N(CH_3)_2$; $n=3$]

The titled compound was synthesized from the compound of Reference Example III-2 in the same manner as in Example 2.

Example 9

4,5-dichloro-1a,7a-dihydro-7(1H)-(3-dimethylaminopropyloxyimino)-1a-phenylcyclopropa[b]chromen [Compound of formula (I) wherein $A^1=4\text{-Cl}$; $A^2=5\text{-Cl}$; $B^1=H$; $B^2=H$; $NR^1R^2=N(CH_3)_2$; $n=3$]

The titled compound was synthesized from the compound of Reference Example III-3 in the same manner as in Example 2.

Example 10

1a,7a-dihydro-4,5-dimethoxy-7(1H)-(3-dimethylaminopropyloxyimino)-1a-phenylcyclopropa[b]chromen [Compound of formula (I) wherein $A^1=4\text{-OCH}_3$; $A^2=5\text{-OCH}_3$; $B^1=H$; $B^2=H$; $NR^1R^2=N(CH_3)_2$; $n=3$]

The titled compound was synthesized from the compound of Reference Example III-1 in the same manner as in Example 2.

Example 11

4,5-dibenzyloxy-1a,7a-dihydro-7(1H)-(3-dimethylaminopropyloxyimino)cyclopropa[b]chromen [Compound of formula (I) wherein $A^1=4\text{-OCH}_2\text{-}C_6H_5$; $A^2=5\text{-OCH}_2\text{-}C_6H_5$; $B^1=H$; $B^2=H$; $NR^1R^2=N(CH_3)_2$; $n=3$]

The titled compound was synthesized from the compound of Reference Example III-4 in the same manner as in Example 2.

Example 12

1a,7a-dihydro-4,5-dihydroxy-7(1H)-(3-dimethylaminopropyloxyimino)cyclopropa[b]chromen [Compound of formula (I) wherein $A^1=4\text{-OH}$; $A^2=5\text{-OH}$; $B^1=H$; $B^2=H$; $NR^1R^2=N(CH_3)_2$; $n=3$]

In 20 ml of ethyl acetate was suspended 48 mg of 10% palladium-on-carbon. After displacing the atmosphere with hydrogen by suction, 240 mg of the compound obtained in Example 11 was added to the suspension, and the mixture was stirred at room temperature for 5 hours in a hydrogen stream (atmospheric pressure). The reaction mixture was worked-up in the same manner as in Example 2 to obtain 67.0 mg (41.5%) of the titled compound.

Physical properties of the compounds obtained in Examples 1 to 12 are shown in Table 4 below.

TABLE 4

| Example | Structure | m.p. (°C) | IR | NMR | Elementary Analysis/MS |
|---|---|---|---|---|---|
| 1 | (3,4-dimethoxyphenyl, phenyl cyclopropane chromene, N-CH₃, NH oxime ether) | 88–89 (L-tartrate) | 2930 2840<br>1600 1500<br>1455 1420<br>1380 1310<br>1260 1215<br>1165 1080<br>1040 860<br>800 755<br>695 | 1.57(t, 1H, J=6.6Hz)<br>1.88(dd, 1H, J=6.6Hz & 10.6Hz)<br>2.49(s, 3H), 2.94(t, 2H, J=5.1Hz)<br>2.97(dd, 1H, J=6.6Hz & 10.6Hz)<br>3.87(s, 3H), 3.89(s, 3H)<br>4.31(t, 2H, J=5.1Hz)<br>6.49(s, 1H)<br>7.22–7.49(m, 6H) | L-tartrate 1 H₂O<br>    C    H    N<br>Calc.: 55.96 6.01 5.22<br>Found: 55.79 6.06 4.91 |
| 2 | (3,4-dichlorophenyl, phenyl cyclopropane chromene, N(CH₃)₂ oxime ether) | 177–179 (Maleate) | 2940 2820<br>2760 1615<br>1465 1402<br>1280 1235<br>1205 1190<br>1122 1035<br>988 885<br>760 742 | 1.45–1.55(m, 1H)<br>1.90(dd, 1H, J=6.6Hz & 10.6Hz)<br>2.31(s, 6H), 2.69(t, 2H, J=6.1Hz)<br>2.99(dd, 1H, J=6.6Hz & 10.6Hz)<br>4.25–4.35(m, 2H) 7.10(s, 1H)<br>7.3–7.45(m, 5H)<br>7.91(s, 1H) | Maleate ½ H₂O<br>    C    H    N<br>Calc.: 56.31 4.82 5.47<br>Found: 56.37 4.70 5.43 |
| 3 | (3,4-dimethoxyphenyl, phenyl cyclopropane chromene, N(CH₃)₂ oxime ether) | 122–125 (Maleate) | 2920 2800<br>2750 1600<br>1500 1445<br>1415 1250<br>1205 1190<br>1160 1080<br>1030 860<br>800 750<br>690 | 1.55(t, 1H, J=6.6Hz)<br>1.85(dd, 1H, J=6.6Hz & 10.6Hz)<br>2.32(s, 6H), 2.70(t, 2H, J=5.9Hz)<br>2.99(dd, 1H, J=6.6Hz & 10.6Hz)<br>3.86(s, 3H), 3.89(s, 3H)<br>4.30(t, 2H, J=5.9Hz)<br>6.49(s, 1H)<br>7.25–7.47(m, 6H) | Maleate<br>    C    H    N<br>Calc.: 62.64 6.07 5.62<br>Found: 62.65 6.17 5.60 |
| 4 | (3,4-dimethoxyphenyl, phenyl cyclopropane chromene, N(CH₂CH₃)₂ oxime ether) | 156–157 (Citrate) | 2950 2810<br>1615 1600<br>1500 1460<br>1450 1420<br>1255 1210<br>1080 1035<br>970 860<br>800 755<br>690 | 1.07(t, 6H, J=7.3Hz)<br>1.55(t, 1H, J=6.6Hz)<br>1.85(dd, 1H, J=6.6Hz & 10.6Hz)<br>2.66(quartett, 4H, J=7.3Hz)<br>2.88(t, 2H, J=6.2Hz)<br>2.98(dd, 1H, J=6.6Hz & 10.6Hz)<br>3.86(s, 3H), 3.89(s, 3H)<br>4.31(t, 2H, J=6.2Hz) 6.49(s, 1H)<br>7.24–7.47(m, 6H) | Citrate ½ H₂O<br>    C    H    N<br>Calc.: 58.91 6.43 4.58<br>Found: 58.86 6.28 4.57 |

TABLE 4-continued

| Example | Structure | m.p. (°C.) | IR | NMR | Elementary Analysis/MS |
|---|---|---|---|---|---|
| 5 | (structure: 3,4-dichlorophenyl cyclopropane-phenyl oxime with N-methylaminopropyl) | (Fumarate) 100–105 | 3435 2955<br>2790 1685<br>1615 1405<br>1285 1240<br>1130 985<br>760 745<br>705 | 1.59(br, 1H)<br>1.95(m, 3H)<br>2.45(s, 3H)<br>2.72(t, 2H, J=7.3Hz)<br>2.96(dd, 1H, J=6.6Hz & 10.6Hz)<br>4.27(m, 2H)<br>7.10(s, 1H)<br>7.4(m, 5H)<br>7.91(s, 1H) | Fumarate ½ H₂O<br>    C    H    N<br>Calc.: 55.82 4.88 5.43<br>Found: 55.69 4.94 5.18 |
| 6 | (structure: 3,4-dimethoxyphenyl cyclopropane-phenyl oxime with N-methylaminopropyl) | 110–115 (L-tartrate) | 2920 1600<br>1500 1460<br>1445 1420<br>1365 1300<br>1255 1205<br>1190 1160<br>1080 1040<br>985 860<br>800 755<br>720 690 | 1.56(t, 1H, J=6.6Hz)<br>1.87(dd, 1H, J=6.6Hz & 10.6Hz)<br>1.94(quintett, 2H, J=6.6Hz)<br>2.44(s, 3H), 2.73(t, 2H, J=6.6Hz)<br>2.96(dd, 1H, J=6.6Hz & 10.6Hz)<br>3.86(s, 3H), 3.89(s, 3H),<br>4.25(t, 2H, J=6.6Hz)<br>6.49(s, 1H)<br>7.23–7.48(m, 7H) | L-tartrate.2 H₂O<br>    C    H    N<br>Calc.: 54.92 6.38 4.93<br>Found: 55.20 6.23 5.40 |
| 7 | (structure: 3,4-dichlorophenyl cyclopropane-phenyl oxime with N-methylaminoethyl) | (Fumarate) 137–140 | 3435 2945<br>2790 1690<br>1615 1405<br>1285 1240<br>1130 985<br>760 745<br>700 | 1.10(t, 3H, J=7.3Hz) 1.52(br, 1H)<br>1.57(t, 1H, J=6.6Hz) 1.9(m, 3H)<br>2.66(q, 2H, J=7.3Hz)<br>2.76(t, 2H, J=7.3Hz)<br>2.96(dd, 1H, J=6.6Hz & 10.6Hz)<br>4.27(m, 2H) 7.10(s, 1H)<br>7.4(m, 5H) 7.91(s, 1H) | Fumarate ½ H₂O<br>    C    H    N<br>Calc.: 57.10 5.08 5.33<br>Found: 57.08 5.06 5.05 |
| 8 | (structure: 2,3-dimethoxyphenyl cyclopropane-phenyl oxime with N,N-dimethylaminopropyl) | 85–90 (Citrate) | 2940 1600<br>1500 1450<br>1420 1380<br>1345 1285<br>1225 1095<br>1030 960<br>795 750<br>720 690 | 1.62(t, 1H, J=6.6Hz)<br>1.8–2.0(m, 3H) 2.25(s, 6H)<br>2.25–2.45(m, 2H)<br>3.02(dd, 1H, J=6.6Hz & 10.6Hz)<br>3.88(s, 6H) J=6.3Hz)<br>4.15–4.3(m, 2H)<br>6.60(d, 1H, J=9.2Hz)<br>7.25–7.6(m, 6H) | Citrate ½ H₂O<br>    C    H    N<br>Calc.: 58.28 6.24 4.69<br>Found: 58.50 6.20 4.68 |

TABLE 4-continued

| Example | Structure | m.p. (°C.) | IR | NMR | Elementary Analysis/MS |
|---|---|---|---|---|---|
| 9 | 3,4-dichlorophenyl chromene with =NO-CH₂CH₂CH₂-N(CH₃)₂ and 2-phenyl cyclopropane | 181–184 (Maleate) | 2940 1615<br>1462 1402<br>1280 1235<br>1122 1040<br>985 | 1.5–1.65(m, 1H)<br>1.85–2.0(m, 3H)<br>2.27(s, 6H)<br>2.97(dd, 1H, J=6.6Hz & 10.6Hz)<br>2.40(t, 2H, J=7.3Hz)<br>4.24(t, 2H) 7.10(s, 1H)<br>7.3–7.45(m, 5H)<br>7.91(s, 1H) | Maleate<br><br>Calc.: C 57.59 H 5.03 N 5.37<br>Found: C 57.49 H 5.08 N 5.34 |
| 10 | 6,7-dimethoxy chromene with =NO-CH₂CH₂CH₂-N(CH₃)₂ and 2-phenyl cyclopropane | 131.0–132.5 (Maleate) | 2950 2860<br>2820 2770<br>1605 1505<br>1465 1420<br>1375 1310<br>1260 1215<br>1200 1160<br>970 865<br>805 760<br>695 | 1.57(t, 1H, J=6.6Hz)<br>1.90(dd, 1H, J=6.6Hz & 10.6Hz)<br>2.30–2.40(m, 2H) 2.78(s, 6H)<br>2.89(dd, 1H, J=6.6Hz & 10.6Hz)<br>3.09–3.18(m, 2H)<br>3.87, 3.90(s, 3H)<br>4.28(t, 2H, J=5.7Hz) 6.50(s, 1H)<br>7.19(s, 1H)<br>7.32–7.49(m, 5H) | Maleate<br><br>Calc.: C 63.27 H 6.29 N 5.47<br>Found: C 63.22 H 6.25 N 5.43 |
| 11 | 6,7-dibenzyloxy chromene with =NO-CH₂CH₂CH₂-N(CH₃)₂ and 2-phenyl cyclopropane | oil | 2930 2860<br>2800 2760<br>1600 1500<br>1440 1370<br>1300 1255<br>1200 1165<br>1080 1035<br>1020 900<br>850 735<br>690 | 1.55(t, 1H, J=6.6Hz)<br>1.84(dd, 1H, J=6.6Hz & 10.6Hz)<br>1.96(quintett, 2H, J=7.0Hz)<br>2.30(s, 6H) 2.50(t, 2H, J=7.0Hz)<br>2.93(dd, 1H, J=6.6Hz & 10.6Hz)<br>4.21(t, 2H, J=7.0Hz)<br>5.09(s, 4H) 6.55(s, 1H)<br>7.25–7.48(m, 16H) | MS<br>448 |
| 12 | 6,7-dihydroxy chromene with =NO-CH₂CH₂CH₂-N(CH₃)₂ and 2-phenyl cyclopropane | oil | 3350 2940<br>1600 1500<br>1450 1380<br>1250 1060<br>1115 980<br>1015 870<br>900 755<br>810 695<br>725 | 1.58(t, 1H, J=6.6Hz)<br>1.83(dd, 1H, J=6.6Hz & 10.5Hz)<br>2.00–2.12(m, 2H) 2.66(s, 6H)<br>2.88(dd, 1H, J=6.6Hz & 10.5Hz)<br>2.97–3.03(m, 2H)<br>4.17–4.25(m, 2H)<br>6.51(s, 1H)<br>7.27–7.44(m, 6H) | MS<br>368 (M⁺) |

Test Example

The compound of the present invention was capable of promoting the extension of nerve dendrites as observed when it was added to a culture cells (NG108-15). Furthermore, it effectively alleviated the defects concerning directional cognition as observed in a model system by performance after the compound had been given to rats suffering from focal resion in the brain, by injection of AF64A into the basal of their forebrain. These effects of the compound of the present invention have been confirmed by the following tests.

(1) Effect of Promoting the Extension of Nerve Dendrites

Method

The effect on the extension of nerve dentrites was examined in accordance with a method reported by Nakagawa et al. [Brain Res., 439, 11–18 (1988)]. A specimen was added to NG108-15 cells which had been cultured in Dulbecco's minimum essential medium (DMEM) containing 5% fetal calf serum at 37° C. under 10% $CO_2$. Three days later, the extension of nerve dendrites was observed under a phase-contrast microscope.

Results

Among the test compounds, those produced in Examples 1, 5, 10, and 12 showed an effect of promoting the extension of nerve dendrites when examined at a concentration of from 1 to 15 $\mu M$.

What is claimed is:

1. A cyclopropachromen represented by formula (I):

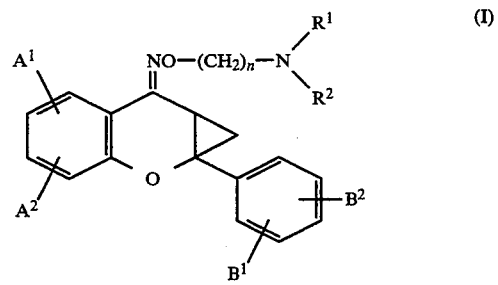

wherein
n represents an integer of 2 to 5;
one of $R^1$ and $R^2$ represents a hydrogen atom or an alkyl group having 1 to 5 carbon atoms, a phenyl group or an aralkyl group having 7 to 10 carbon atoms, and the other of $R^1$ and $R^2$ represents an alkyl group having 1 to 5 carbon atoms, a phenyl group or an aralkyl group having 7 to 10 carbon atoms,
$A^1$ and $A^2$ independently represent a hydroxyl group, a halogen atom, an alkoxy group having 1 to 10 carbon atoms or an alkoxy group having 1 to 10 carbon atoms substituted with phenyl or pyridyl;
$B^1$ and $B^2$ independently represent a hydrogen atom, a hydroxyl group, a halogen atom, an alkoxy group having 1 to 10 carbon atoms or an alkoxy group having 1 to 10 carbon atoms substituted with phenyl or pyridyl, and a pharmaceutically acceptable salt thereof.

2. A compound as claimed in claim 1 wherein one of $R^1$ and $R^2$ represents a hydrogen atom, and the other of $R^1$ and $R^2$ represents an alkyl group having 1 to 5 carbon atoms.

3. A compound as claimed in claim 1 wherein each of $R^1$ and $R^2$ represents an alkyl group having 1 to 5 carbon atoms.

4. A compound as claimed in claim 1 wherein each of $B^1$ and $B^2$ represents a hydrogen atom.

5. A compound as claimed in any of claims 1 to 4 wherein $A^1$ and $A^2$ independently represent an alkoxy group having 1 to 5 carbon atoms or an alkoxy group having 1 to 5 carbon atoms substituted with phenyl or pyridyl.

6. A compound as claimed in any of claims 1 to 4 wherein each of $A^1$ and $A^2$ represents a hydroxyl group.

7. A compound as claimed in any of claims 1 to 4 wherein $A^1$ and $A^2$ independently represent a halogen atom.

* * * * *

UNITED STATES PATENT AND TRADEMARK OFFICE
CERTIFICATE OF CORRECTION

PATENT NO. : 5,401,850
DATED : March 28, 1995
INVENTOR(S) : TATSUOKA et al.

It is certified that error appears in the above-indentified patent and that said Letters Patent is hereby corrected as shown below:

ON THE TITLE PAGE:

Insert --[30] Foreign Priority Data

Jun. 6, 1990 [JP] Japan...................147710/1990--

Signed and Sealed this

Eighteenth Day of July, 1995

*Attest:*

BRUCE LEHMAN

*Attesting Officer*     *Commissioner of Patents and Trademarks*